US00PP14605P29

(12) United States Plant Patent
Pierce

(10) Patent No.: US PP14,605 P2
(45) Date of Patent: Mar. 16, 2004

(54) CALIBRACHOA PLANT NAMED 'CAL SUNRE'

(50) Latin Name: *Calibrachoa spp.*
Varietal Denomination: Cal Sunre

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 28 days.

(21) Appl. No.: 10/389,041

(22) Filed: Mar. 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—Jondle & Associates, PC

(57) ABSTRACT

'Cal Sunre' is a new variety of Calibrachoa plant. This new variety has a golden yellow background with scarlet variegation colored flowers.

1 Drawing Sheet

Genus and species: Calibrachoa spp.
Variety denomination: 'Cal Sunre'.

BACKGROUND OF THE INVENTION

'Cal Sunre' originated from a hybridization made in the year 2000 in Gilroy, Calif. The female parent was a Calibrachoa breeding line with yellow colored flowers known as Million Bells Yellow a commercial patented (U.S. Plant Pat. No. 11,558) line. The male parent was Calibrachoa variety 16-1, a scarlet red proprietary line unnamed and unpatented.

'Cal Sunre' is a product of a planned breeding program intended to create new calibrachoa plants with a golden yellow background with scarlet variegation colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a 2 and half-year period. The plant has also been trialed at Gilroy, Calif., Litchfield, Mich. and Andijk, The Netherlands. The present invention has been found to retain its distinctive characteristics through successive propagations; and this novelty is firmly fixed.

Description of the genus Calibrachoa Llave & Lex

The genus Petunia was originally established in 1803 by A. L. Jussieu, who described both, *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida,* the Garden Petunia, and the inter-relationship of several species classified as Petunia. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

BRIEF DESCRIPTION OF THE PHOTOGRAPH

The accompanying colored photograph, illustrates the overall appearance of the cultivar Cal Sunre, showing the colors as true as it is reasonably possible to obtain in colored reproduction of this type.

DETAILED DESCRIPTION OF THE NEW PLANT

The following traits and characteristics describe the new variety. The plant history was taken on 10 month old plants that were cut back numerous times prior to data readings being taken.

Classification:
*Family.*—Solanaceae.
*Species.*—Calibrachoa spp.
Growth:
*Form.*—Semi upright and decumbent.
*Habit.*—Good vigorous habit, well branched, full plant.
*Height.*—15–25 cm.
*Width.*—50–60 cm.
*Time to produce a finished flowering plant.*—9–11 weeks.
*Outdoors plant performance.*—Full sun, free flowering through the summer, some heat tolerance, used as a hanging plant, in mixed container plantings, mass planting in a bed.
*Time to initiate and develop roots.*—18–23 days.
*Rood description.*—White, fibrous.
Stems:
*Stem color.*—RHS 144A (yellow-green).
*Stem length.*—60–80 cm.
*Stem diameter.*—0.2 cm.
*Stem internodes length.*—3.0–5.0 cm.
*Stem texture.*—Very short glandular hairs of various sizes.
*Stem anthocyanin.*—No.
*Pedicel color.*—RHS 144A (yellow-green).
*Pedicel length.*—1.8–2.8 cm.
*Pedicel diameter.*—0.1 cm.
*Pedicel texture.*—Many glandular hairs of various sizes.
Leaves:
*Arrangement.*—Alternate, upper leaves sub-opposite.
*Leaf color.*—Upper side, RHS 137A (green). Underside, RHS 137C (green).
*Leaf length.*—2.7–3.2 cm.
*Leaf width.*—1.1–1.3 cm.
*Leaf blade shape.*—Elliptic.
*Leaf margin.*—Entire.
*Leaf apex aspect.*—Obtuse.
*Leaf bas aspect.*—Acuminate.
*Leaf texture.*—Many glandular hairs of various sizes.
*Venation.*—Pinnate.
*Venation color.*—RHS 144B (yellow-green).
*Petiole color.*—RHS 144B (yellow-green).
*Petiole length.*—0.2 cm.
*Petiole width.*—0.15 cm.
*Petiole texture.*—Many glandular hairs of various sizes.
Bud:
*Color at tight bud.*—RHS 160B (greyed-yellow).
*Bud shape.*—Oblong.
*Bud diameter.*—0.4–0.5 cm.
*Bud length.*—1.3–1.8 cm.
Flowers:
*Blooming habit.*—Continuous throughout the growing season. Good floriferousness.
*Inflorescence type.*—Flowers solitary in upper leaf axis.
*Floret type.*—Funnel form, 5 lobed petals, fused at base.
*Young flower color.*—RHS 5B (yellow) base color; very heavily, irregularly, overlaid with RHS 34A (orange-red) and RHS 45A (red) in striated form, and a blush of RHS N34A (orange-red) at the flare; RHS 166A (greyed-orange) mid-veins.
*Floret diameter.*—2.0–2.4 cm.
*Mature flower color.*—Front side, RHS 9A (yellow) base color, with very heavily, irregularly overlaid, RHS 33A (orange-red) in striated form, and a blush of RHS 44A (red) at the flare; light intensity of RHS 177C (greyed-orange) mid-veins, slightly darker than the flare.
*Mature flower color.*—Underside, RHS 38A and B (red), irregularly mingled with RHS 10C (yellow) mainly at the mid-veins; RHS 166A (greyed-orange) mid-veins.
*Corolla tube color inside.*—Between RHS 13A/B (yellow) base color; RHS N199B (greyed-brown) mid-veins; RHS 199A (greyed-brown) secondary veining.
*Corolla tube length.*—1.8–2.0 cm.
*Corolla outside texture.*—Many glandular hairs of various sizes.
*Flower (limb) diameter.*—2.8–3.1 cm.
*Petal apex shape.*—Irregularly, macronlate to rounded.
*Petal base shape.*—Fused.
*Petal margin.*—Entire.
*Waviness of petals.*—Weak.
*Petal lobation.*—Slightly moderate.
*Petal texture.*—Papillose.
*Sepals.*—5, fused at base.
*Sepal color.*—RHS 137A (green).
*Sepal length.*—1.1–1.5 cm.
*Sepal width.*—0.3 cm.
*Sepal shape.*—Oblong.
*Sepal apex.*—Acute.
*Sepal texture.*—Many glandular hairs of various sizes.
*Lastingness of individual blooms.*—5–8 days.
*Fragrance.*—None.
Reproductive organs:
*Stamens.*—5, 2 taller, 3 shorter.
*Filament color.*—RHS 150D (yellow-green).
*Pollen color.*—RHS 6A (yellow).
*Pistil.*—One.
*Stigma color.*—RHS 143B (green).
*Style color.*—RHS 145B (yellow-green).
*Fruit seed set.*—Not observed.

Disease and Insect Resistance

Not observed.

COMPARISON WITH MOST SIMILAR VARIETY

'Cal Sunre' differs from the female parent MB Yellow in the following ways: 257-2 has a golden yellow background with scarlet variegation and MB Yellow has yellow flowers. 257-2 has larger flowers and flowers earlier than MB Yellow.

'Cal Sunre' differs from the male parent 16-1 in the following ways: 257-2 has a golden yellow background with scarlet variegation and 16-1 has solid orange scarlet flowers. 257-2 is more center flowered and is more basal branching than 16-1.

What is claimed is:

1. A new and distinct Calibrachoa plant, as shown and described herein.

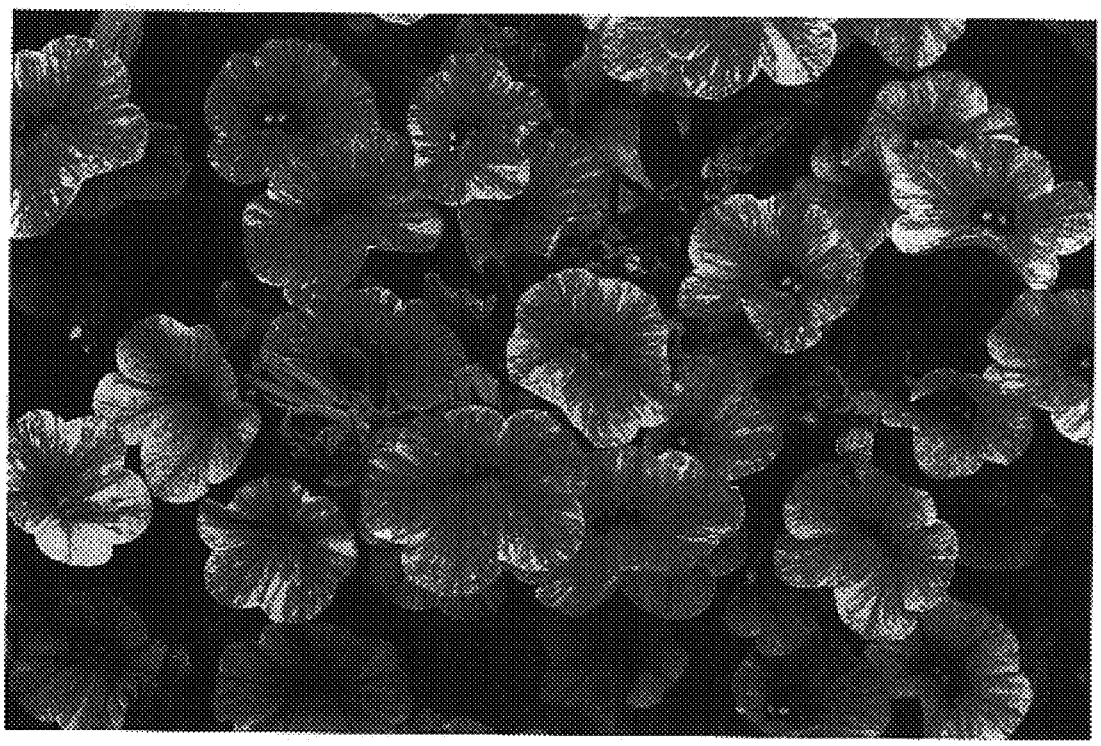

* * * * *